(12) United States Patent
Fujinami et al.

(10) Patent No.: US 8,986,896 B2
(45) Date of Patent: Mar. 24, 2015

(54) ELECTROLYTE SOLUTION AND USE THEREFOR

(75) Inventors: Tatsuo Fujinami, Hamamatsu (JP); Tatsuya Koga, Yokohama (JP)

(73) Assignees: Toyota Jidosha Kabushiki Kaisha, Toyota-shi, Aichi (JP); National University Corporation Shizuoka University, Shizuoka-shi, Shizuoka (JP)

( * ) Notice: Subject to any disclaimer, the term of this patent is extended or adjusted under 35 U.S.C. 154(b) by 467 days.

(21) Appl. No.: 13/061,968

(22) PCT Filed: Sep. 10, 2009

(86) PCT No.: PCT/JP2009/065845
§ 371 (c)(1),
(2), (4) Date: Jun. 3, 2011

(87) PCT Pub. No.: WO2010/029971
PCT Pub. Date: Mar. 18, 2010

(65) Prior Publication Data
US 2011/0229772 A1    Sep. 22, 2011

(30) Foreign Application Priority Data
Sep. 11, 2008  (JP) .................................. 2008-233366

(51) Int. Cl.
*H01M 6/16* (2006.01)
*H01M 6/00* (2006.01)
(Continued)

(52) U.S. Cl.
CPC ......... *H01M 10/0566* (2013.01); *C07D 307/00* (2013.01); *H01M 4/587* (2013.01);
(Continued)

(58) Field of Classification Search
CPC ............ C07C 307/00; H01M 10/0566; H01M 10/0568; H01M 10/0569; H01M 10/052; Y02E 60/122
USPC .......... 429/122, 126, 188, 337; 568/942, 583, 568/538, 379, 376, 300; 423/289
See application file for complete search history.

(56) References Cited

U.S. PATENT DOCUMENTS 4,118,550 A * 10/1978 Koch ............................ 429/328
6,045,948 A    4/2000 Wang et al.
(Continued)

FOREIGN PATENT DOCUMENTS

EP    2 063 482 A1    5/2009
EP    2063482    *    5/2009  ............ H01M 10/40
(Continued)

OTHER PUBLICATIONS

Wirth et al. Journal of Physical Chemistry 1962 vol. 66 No. 11 pp. 2277-2279.*
(Continued)

*Primary Examiner* — Patrick Ryan
*Assistant Examiner* — Aaron Greso
(74) *Attorney, Agent, or Firm* — Finnegan, Henderson, Farabow, Garrett & Dunner, LLP

(57) ABSTRACT

The present invention provides an electrolyte solution including: a solvent composed primarily of a $BF_3$-cyclic ether complex; and a supporting electrolyte. For example, preferred is an electrolyte solution in which the cyclic ether is one or two or more selected from optionally substituted tetrahydrofuran and optionally substituted tetrahydropyran.

10 Claims, 5 Drawing Sheets

10μm

(51) Int. Cl.

| | |
|---|---|
| *H01M 10/00* | (2006.01) |
| *H01M 6/04* | (2006.01) |
| *H01M 10/12* | (2006.01) |
| *C01B 25/08* | (2006.01) |
| *C01B 35/02* | (2006.01) |
| *C07C 43/00* | (2006.01) |
| *C07C 205/00* | (2006.01) |
| *C07C 49/00* | (2006.01) |
| *C07F 15/00* | (2006.01) |
| *H01M 10/0566* | (2010.01) |
| *C07D 307/00* | (2006.01) |
| *H01M 4/587* | (2010.01) |
| *H01M 10/052* | (2010.01) |
| *H01M 10/0568* | (2010.01) |
| *H01M 10/0569* | (2010.01) |

(52) U.S. Cl.
CPC ........ H01M10/052 (2013.01); H01M 10/0568 (2013.01); H01M 10/0569 (2013.01); *H01M 2300/0025* (2013.01); *Y02E 60/122* (2013.01)
USPC .......... 429/337; 429/122; 429/126; 429/188; 568/583; 568/379; 568/376; 568/300; 423/289

(56) References Cited

U.S. PATENT DOCUMENTS

| | | | |
|---|---|---|---|
| 7,833,660 B1 * | 11/2010 | Zhang et al. | 429/188 |
| 2005/0186469 A1 * | 8/2005 | De Jonghe et al. | 429/137 |
| 2006/0073391 A1 * | 4/2006 | Kim | 429/329 |

FOREIGN PATENT DOCUMENTS

| | | | | |
|---|---|---|---|---|
| JP | 2-262270 | | 10/1990 | |
| JP | 11026017 | * | 1/1999 | ............ H01M 10/40 |
| JP | 11-149943 | | 6/1999 | |
| JP | 2000-138072 | | 5/2000 | |
| JP | 2008-94825 | | 4/2008 | |
| JP | 2008-273893 | | 11/2008 | |
| WO | WO 2008/032795 A1 | | 3/2008 | |
| WO | WO2008032795 | * | 3/2008 | ............ H01M 10/40 |

OTHER PUBLICATIONS

Xu Chemical Reviews 2004 vol. 104 pp. 4303-4417.*
McLaughlin et al. (Journal of Inorganic and Nuclear Chemistry vol. 17 pp. 112-119 1961.*
Delsignore et al J Physical Chemistry 1984 vol. 88 pp. 2405-2411.*
Gabrisch et al Abstract of Prodeedings Electrochemical Society 2004 2003—28 Lithium and lithium ion batteries pp. 89-94.*
English translation of International Preliminary Report on Patentability in International Application No. PCT/JP2009/065845; Mailing Date: Apr. 14, 2011.
International Search Report in International Application No. PCT/JP2009/065845; Mailing Date: Nov. 17, 2009.

* cited by examiner

10μm

10μm

10μm

ELECTROLYTE SOLUTION AND USE THEREFOR

TECHNICAL FIELD

The present invention relates to an electrolyte solution useful as a component of a lithium secondary battery or other electrochemical device.

This application is a national phase application of International Application No. PCT/JP2009/065845, filed Sep. 10, 2009, and claims priority to Japanese Patent Application No. 2008-233366 filed on Sep. 11, 2008, the entire contents of both of which are incorporated herein by reference.

BACKGROUND ART

In general, electrolyte solutions used in batteries and other electrochemical devices preferably have the property of resistance to oxidation and reduction. In other words, they are preferably electrolyte solutions with broad potential windows. For example, electrolyte solutions used in lithium secondary batteries have conventionally comprised lithium salts (supporting salts) dissolved in carbonate solvents such as ethylene carbonate, propylene carbonate, diethyl carbonate and the like, but from the standpoint of improving the performance of lithium secondary batteries, electrolyte solutions using solvents that are more resistant to oxidation than carbonate solvents would be preferable.

Boron trifluoride ($BF_3$) exhibits strong acidity because the boron atom is bound to three strongly electron-withdrawing fluorine atoms. In a $BF_3$ complex comprising an organic molecule coordinated with the unoccupied orbital of the boron in $BF_3$, it is expected that the oxidation resistance of the organic molecule will be improved because electrons of the coordinated organic molecule are drawn towards the boron atom due to the strong electron-withdrawing properties of the $BF_3$ part of the complex. Japanese Patent Application Laid-open No. 2008-94825 (Patent Document 1) describes an electrolyte solution containing a $BF_3$ complex comprising a chain ether such as dimethoxyethane coordinated with $BF_3$. In Japanese Patent Applications Laid-open Nos. H11-149943 and 2000-138072 (Patent Documents 2 & 3), $BF_3$ complexes are only used in small amounts as additives to electrolytes, and are not themselves used as electrolytes. Japanese Patent Application Laid-open No. H02-262270 (Patent Document 4) describes a battery having as a component an organic electrolyte solution comprising $BF_3$ or another compound having a B—F bond added to an organic electrolyte solution obtained by dissolving a lithium salt in an organic solvent containing a cyclic ether, but this electrolyte solution does not use a complex of $BF_3$ or the like with an ether. Patent Document 4 describes the possibility of solvation between the $BF_3$ or the like and the ether, but there is an obvious difference between solvation and complex formation.

Patent Document 1: Japanese Patent Application Laid-open No. 2008-94825
Patent Document 2: Japanese Patent Application Laid-open No. H11-149943
Patent Document 3: Japanese Patent Application Laid-open No. 2000-138072
Patent Document 4: Japanese Patent Application Laid-open No. H02-262270

DISCLOSURE OF THE INVENTION

The inventors in this case discovered that in a lithium-ion battery using graphite as the negative electrode active material, in some cases the layered structure of the graphite is damaged by charge-discharge of the battery when using an electrolyte solution comprising a supporting electrolyte dissolved in a complex of a chain ether coordinated with $BF_3$ ($BF_3$-chain ether complex). This damage to the graphite structure can be a cause of lower capacity and decreased durability of the lithium ion battery. This damage to the graphite structure is not observed with electrolyte solutions containing only small amounts of $BF_3$-chain ether complexes as additives, but is a new problem that has occurred for the first time with electrolyte solutions containing high levels of such complexes as solvents.

It is an object of the present invention to provide an electrolyte solution that has a $BF_3$ complex as the principal solvent, but that is unlikely to damage the graphite structure. It is another object of the present invention to provide a method for manufacturing this electrolyte solution, and a battery provided with the electrolyte solution.

The present invention provides an electrolyte solution including a solvent; and a supporting electrolyte. The solvent is composed primarily of a $BF_3$-cyclic ether complex comprising a cyclic ether coordinated with $BF_3$. This $BF_3$-cyclic ether complex exhibits higher oxidation resistance than the cyclic ether by itself (not forming a $BF_3$ complex). Consequently, an electrolyte solution having this complex as a principal component of the solvent (that is, as the principal solvent) can have a broader potential window. This electrolyte solution is useful as an electrolyte solution for use in various electrochemical devices (such as batteries). Moreover, while damage to the graphite as discussed above has been observed with electrolyte solutions comprising supporting electrolytes dissolved in $BF_3$-dimethyl ether complexes and other chain ether complexes, such damage is prevented or reduced with the electrolyte solution of the present invention. This is attributed partly to the fact that cyclic ether structures are bulkier than chain ether structures, making it more difficult for the $BF_3$-cyclic ether complex to penetrate between layers of graphite. Consequently, the electrolyte solution of the present invention is especially desirable for use in batteries (such as lithium-ion batteries) in which the electrode active material is a carbon material having at least a partial graphite structure, and is also useful as an electrolyte solution for a variety of other electrochemical devices.

The cyclic ether constituting the $BF_3$-cyclic ether complex may for example be one or two or more selected from optionally substituted tetrahydrofuran and optionally substituted tetrahydropyran. In a preferred embodiment, the cyclic ether is one or two or more selected from tetrahydrofuran (THF), 2-methyltetrahydrofuran (2MeTHF) and tetrahydropyran (THP). These cyclic ethers can be easily obtained or synthesized. Of these, 2MeTHF and THP (particularly THP) are desirable because they can form a $BF_3$ complex with superior oxidation resistance.

The present invention provides a battery (typically a secondary battery) provided with any of the electrolyte solutions disclosed here. In particular, this battery is preferably constructed using a carbon material having a graphite structure as an electrode active material. The effects (such as the effect of controlling damage to the graphite structure) of using the electrolyte solution of the present invention are better obtained with such a battery. A desirable example of a battery provided with this electrolyte solution is a lithium secondary battery using a lithium salt as the supporting electrolyte and a carbon material having a graphite structure as an electrode active material (typically the negative electrode active material).

The present invention also provides a method for manufacturing any of the electrolyte solutions disclosed here. This method includes mixing the cyclic ether with a $BF_3$-exchangeable ether complex (for example, a $BF_3$-diethyl ether complex) comprising $BF_3$ coordinated with an exchangeable ether other than the cyclic ether, and then removing the exchangeable ether from the reaction system to obtain the $BF_3$-cyclic ether complex. It also includes mixing the $BF_3$-cyclic ether complex with the supporting electrolyte. By this method, it is possible to easily synthesize various $BF_3$-cyclic ether complexes by means of an ether exchange reaction using any $BF_3$-exchangeable ether complex (preferably a complex that is liquid at room temperature and easy to obtain or synthesize) and a cyclic ether corresponding to the structure of the target $BF_3$-cyclic ether complex.

BEST MODE FOR CARRYING OUT THE INVENTION

Figure 1:
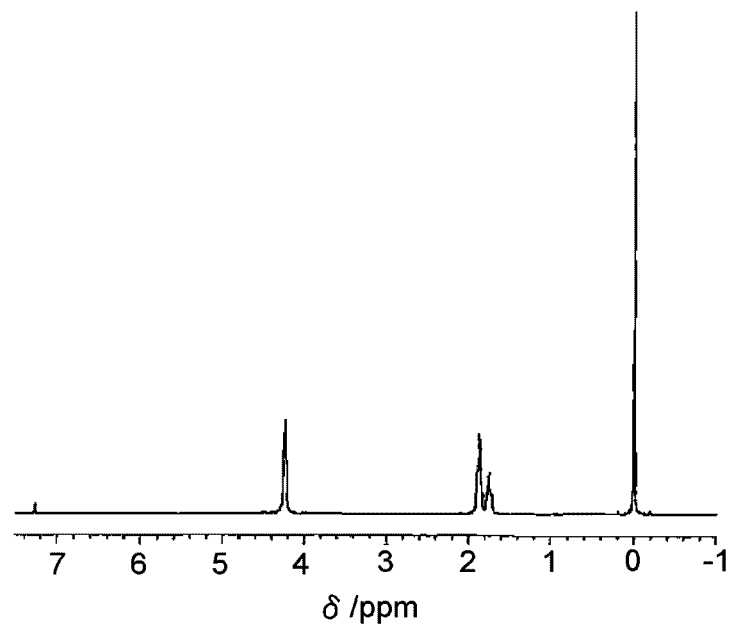
FIG. 1 shows the $^1$H-NMR spectrum of a $BF_3$-THP complex.

Preferred embodiments of the present invention are explained in detail below. Technical matters not specifically mentioned in this Description that are necessary for implementing the present invention can be understood as design matters by a person skilled in the art based on prior art. The present invention can be implemented based on the content disclosed in this Description and on technical common knowledge in the field.

It is a feature of the electrolyte solution disclosed here that the principal solvent is a $BF_3$-cyclic ether complex. That is, the principal component or in other words at least 50 mass % of the solvent in the electrolyte solution consists of one or two or more $BF_3$-cyclic ether complexes. A $BF_3$-cyclic ether complex here means a complex having a $BF_3$ part and a cyclic ether part, wherein lone electron pairs of the oxygen atoms in the ether ring are coordinated with the unoccupied orbits of the boron atom of the $BF_3$ part. The structure of this complex can be identified by a method such as $^{13}$C-NMR measurement, $^1$H-NMR measurement or the like. Complex formation between the ether and $BF_3$ (as opposed to simple solvation for example) can be confirmed from the chemical shift in the NMR spectrum.

The ether ring is a structural part having at least one etheric oxygen as a constituent atom of the ring. The number of atoms in the ether ring is preferably 5 to 8 or more preferably 5 or 6. The cyclic ether part may have two or more etheric oxygen atoms as constituent atoms of the ring, and may also have sulfur (S), nitrogen (N) and other hetero atoms in addition to etheric oxygen. Preferably it has a single etheric oxygen as a constituent atom, with the remainder being carbon atoms. It may be either a saturated cyclic ether or unsaturated cyclic ether, but is preferably a saturated cyclic ether. This ether ring may have one or two or more substituents bound to the ring, or may be unsubstituted. When there are substituents, examples of suitable substituents include $C_{1-6}$ (preferably $C_{1-3}$, or more preferably $C_{1-2}$, or typically $C_1$) alkyl groups and alkoxy groups.

There may be one or two or more $BF_3$-cyclic ether complexes selected from the group consisting of the following Formulae (1) through (6) for example.

[C1]

(1)

[C2]

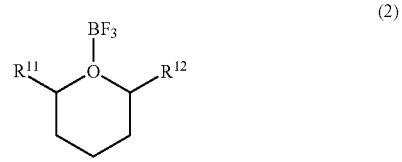

(2)

(in the formula, $R^{11}$ is any selected from the $C_{1-3}$ alkyl groups and $C_{1-3}$ alkoxy groups, and $R^{12}$ is any selected from a hydrogen atom and the $C_{1-3}$ alkyl groups and $C_{1-3}$ alkoxy groups.

[C3]

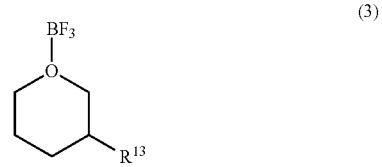

(3)

(in the formula, $R^{13}$ is selected from the $C_{1-3}$ alkyl groups).

[C4]

(4)

[C5]

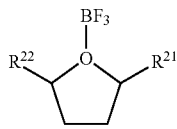

(5)

(in the formula, $R^{21}$ is any selected from the $C_{1-3}$ alkyl groups and $C_{1-3}$ alkoxy groups, and $R^{22}$ is any selected from a hydrogen atom and the $C_{1-3}$ alkyl groups and $C_{1-3}$ alkoxy groups.)

[C6]

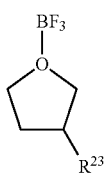

(6)

(in the formula, $R^{23}$ is any selected from the $C_{1-3}$ alkyl groups).

A $BF_3$ complex of a cyclic ether having no substituents on the ether ring as in Formulae (1) and (4) is advantageous from a manufacturing standpoint because such cyclic ethers are easy to obtain. Of these, an electrolyte solution containing the $BF_3$-tetrahydropyran complex represented by Formula (1) as a solvent (typically a principal solvent) is desirable because it may have an oxidizing potential much greater than 5 V. This electrolyte solution is useful for example as an electrolyte solution for use in 5 V batteries.

In the case of a $BF_3$ complex of a cyclic ether having one or two or more substituents on the ether ring as in Formulae (2), (3), (5) and (6), the cyclic ether part is much bulkier than when no substituents are present. Thus, damage to the graphite can be prevented to a greater degree using an electrolyte solution containing such a $BF_3$ complex as a solvent (typically a principal solvent). Introducing a substituent into a cyclic ether having no substituent breaks the symmetry of the molecule, reducing its crystallinity and thereby lowering its melting point. Therefore, a $BF_3$ complex of a substituted cyclic ether may have a lower melting point than a $BF_3$ complex of an unsubstituted cyclic ether. A $BF_3$-cyclic ether complex with a lower melting point is advantageous from the standpoint of the low-temperature characteristics of an electrolyte solution containing the complex as a solvent (typically a principal solvent). The oxidation potential can also be increased over that obtained with an unsubstituted cyclic ether by introducing such substituents.

The $BF_3$-cyclic ether complex in the electrolyte solution disclosed here can be manufactured for example by aerating an organic raw material (typically, a cyclic ether corresponding to the structure of the target complex) with $BF_3$ gas.

In a preferred method for manufacturing the $BF_3$-cyclic ether complex, a cyclic ether corresponding to the target $BF_3$-cyclic ether complex is first mixed with a $BF_3$-exchangeable ether complex comprising $BF_3$ coordinated with an exchangeable ether other than the cyclic ether, after which the exchangeable ether is removed from the reaction system. This method uses an ether exchange reaction between the $BF_3$-exchangeable ether complex and the cyclic ether. One advantage of this manufacturing method is that the materials are easier to handle than in the aforementioned method using aeration with $BF_3$ gas.

A manufacturing method using the aforementioned ether exchange reaction is explained in detail here using the manufacture of the $BF_3$-THP complex represented by Formula (4) above as an example. A $BF_3$-diethyl ether complex ($BF_3$-exchangeable ether complex) is mixed with THP (cyclic ether corresponding to target structure), and the diethyl ether part of the $BF_3$-diethyl ether complex is replaced with THP to thereby synthesize the target $BF_3$-THP complex. In more detail, the $BF_3$-diethyl ether complex and THP are mixed (mixing step), and the mixture is stirred in an inert gas (such as argon gas) atmosphere, and then heated under reduced pressure to distill off the diethyl ether from the reaction system (removal step).

The $BF_3$-exchangeable ether complex is preferably one that is liquid at room temperature. "Liquid at room temperature" hear means a fluid state at 25° C. This $BF_3$-exchangeable ether complex is desirable because it is easy to mix with the cyclic ether (which is typically liquid at room temperature), and also easy to handle. Because the ether part of the $BF_3$-exchangeable ether complex is removed (distilled off under reduced pressure for example) from the reaction system in the aforementioned removal step, it is desirable to use a $BF_3$-exchangeable ether complex in which the $BF_3$ is coordinated with an ether that is easy to remove in the removal step. This exchangeable ether is preferably one with a boiling point of −50° C. to 70° C. for example, although this is not a special limitation. An exchangeable ether with a molecular weight in the range of 40 to 200 (preferably 46 to 150) is also desirable.

The preferred type of exchangeable ether will differ depending on the type of cyclic ether to be substituted and the like, but normally diethyl ether or dimethyl ether can be used by preference. It is especially desirable to use diethyl ether. $BF_3$-diethyl ether complexes are commercially available.

In the aforementioned mixing step, the mixing ratio of the $BF_3$-exchangeable ether complex and the cyclic ether is not particularly limited. The molar ratio of $BF_3$-exchangeable ether complex to cyclic ether can normally be about 1:0.5 to 1:2.0, and a ratio of about 1:0.9 to 1:1.5 (typically 1:1 to 1:1.3) is preferred. The $BF_3$-cyclic ether complex can be produced efficiently by mixing the cyclic ether in more than the necessary amount (that is, in an excess of 5 to 30 mole %) with the $BF_3$-exchangeable ether complex.

The temperature for stirring the mixture after mixing the $BF_3$-exchangeable ether complex with the cyclic ether is not particularly limited. Normally a temperature at which the reaction system can maintain a liquid state (or in other words a temperature at which the ether exchange reaction can occur as a liquid-phase reaction) is suitable, and a temperature of about 0° C. to 80° C. can be adopted by preference. From the standpoint of energy cost, and the like, the mixture can be stirred at room temperature (typically about 10° C. to 30° C.), or it can be stirred under warming conditions (such as 35° C. to 60° C.) so as to promote the ether exchange reaction.

In the removal step, the exchangeable ether part of the $BF_3$-exchangeable ether complex can be removed from the reaction system by a method using a flow of an inert gas such as nitrogen or argon gas, by a heating method, or by a method using reduced pressure or the like for example. A suitable combination of these methods can also be used.

Examples of inert gasses that can be used in the method of removal by passage of inert gas include nitrogen gas and argon gas. The mixture is preferably stirred at about room temperature to 60° C. during passage of the inert gas. The stirring time is not particularly limited, but 50 hours or more (such as 50 to 150 hours) is normally suitable. In the method of removal by heating, the preferred heating temperature differs according to the kind of $BF_3$-exchangeable ether complex and cyclic ether used, but can normally be in the range of 40° C. to 90° C. In the method of removal by reduced pressure, the pressure level differs according to the kind of $BF_3$-exchangeable ether complex and cyclic ether used, but can normally be about $2.5\times10^4$ to $700\times10^4$ Pa (about 200 mmHg to 500 mmHg).

The electrolyte solution of the present invention contains any of the $BF_3$-cyclic ether complexes disclosed here (which may be a $BF_3$-cyclic ether complex manufactured by any of the methods disclosed here) as a principal solvent. The $BF_3$-cyclic ether complex preferably constitutes at least 60 mass % or more preferably at least 75 mass % or still more preferably at least 90 mass % of the solvent portion of the electrolyte solution. The $BF_3$-cyclic ether complex may also constitute effectively all of the solvent. When multiple $BF_3$-cyclic ether complexes with different cyclic ether structures are included, the total of content of these as a percentage of the solvent is preferably within the aforementioned range.

The electrolyte solution disclosed here may also contain a solvent other than the $BF_3$-cyclic ether complex as an accessory component (accessory solvent). For example, when the melting point of the $BF_3$-cyclic ether solvent is higher than 10° C. (or in a composition containing multiple $BF_3$-cyclic ether complexes, if the mixture of complexes coagulates at 10° C. or more), it is desirable to use as an accessory solvent a solvent with a melting point lower than that of the $BF_3$-cyclic ether complex. It is desirable to use a solvent that is uniformly miscible with the $BF_3$-cyclic ether complex.

Examples of materials that can be used as this accessory solvent include ethylene carbonate (EC), propylene carbonate (PC), dimethyl carbonate (DMC), diethyl carbonate (DEC), ethylmethyl carbonate (EMC) and other carbonates; ethylmethyl ether, dipropyl ether and other ethers; methoxypropionitrile, acetonitrile and other nitriles; methyl acetate and other esters; triethylamine and other amines; methanol and other alcohols; and acetone and other ketones and the like. One of these may be used alone, or a combination of two or more may be used. Of these, one or two or more selected from the carbonates can be used by preference. A cyclic ether can also be used as the accessory solvent. For example, in addition to the $BF_3$-cyclic ether complex used as the principal solvent, the electrolyte solution may also contain the cyclic ether of this complex as an accessory solvent. Other examples of materials that may be used as accessory solvents include $BF_3$ complexes comprised of organic substances other than cyclic ethers (such as chain ethers) coordinated with $BF_3$.

The supporting electrolyte contained in the electrolyte solution disclosed here can be any that dissolves in a solvent having the aforementioned $BF_3$-cyclic ether complex as a principal solvent, without any particular limitations. This electrolyte solution can be one containing a supporting electrolyte suited to the application. For example, various lithium salts, sodium salts, tertiary ammonium salts and the like can be used as the supporting electrolyte. An electrolyte solution containing a lithium salt as a supporting electrolyte is especially desirable. An electrolyte solution of this composition can be useful as the electrolyte solution of a lithium secondary battery (lithium-ion battery or the like).

Various lithium salts that are known to function as supporting electrolytes in the electrolyte solutions of lithium secondary batteries can be used as the aforementioned lithium salt. The electrolyte solution disclosed here may be an electrolyte solution containing one or two or more lithium salts selected from $LiPF_6$, $LiBF_4$, $LiN(SO_2CF_3)_2$ (sometimes represented as "LiTFSI"), $LiN(SO_2C_2F_5)_2$ (sometimes represented hereunder as "LiBETI"), $LiCF_3SO_3$, $LiC_4F_9SO_3$, $LiC(SO_2CF_3)_3$, $LiClO_4$ and the like as supporting electrolytes.

The concentration of the supporting electrolyte is not particularly limited, but a concentration at which the supporting electrolyte can dissolve stably (with no precipitation of the electrolyte for example) at temperatures of at least 25° C. is normally preferred. For example, an electrolyte solution containing about 0.1 mole or more (such as about 0.1 to 3 moles) of supporting electrolyte in 1 kg of electrolyte solution is preferred, and an electrolyte containing 0.2 moles or more (such as about 0.2 to 2 moles) is more preferred.

An electrolyte solution of such a composition can preferably be prepared for example by preparing the $BF_3$-cyclic ether complex and then mixing this complex with the supporting electrolyte. The $BF_3$-cyclic ether complex can be prepared for example by using the aforementioned ether exchange reaction to manufacture the $BF_3$-cyclic ether complex. When the $BF_3$-cyclic ether complex is used in combination with another solvent as the solvent of the electrolyte solution, this mixed solvent can be mixed with the supporting electrolyte. Alternatively, the lithium salt can be dissolved in part of the solvent components, and this lithium solution can then be mixed with the remaining solvent components. This mixing operation is preferably performed in a dry inert gas (such as nitrogen gas) atmosphere.

The electrolyte solution disclosed here can be used as an electrolyte solution in various electrochemical devices (batteries, sensors and the like). It is preferably used as the electrolyte solution of a battery. "Battery" is a general term for storage devices capable of yielding electrical energy, including both primary batteries and secondary batteries. "Secondary battery" is a general term encompassing lithium secondary batteries, nickel hydrogen batteries, nickel cadmium batteries and other storage batteries as well as electrical double layer capacitors and other storage elements. The electrolyte solution is particularly suitable as the electrolyte solution of a lithium secondary battery (typically a lithium-ion battery).

In general, this lithium secondary battery is configured with a negative electrode and a positive electrode provided with an electrode active material capable of storing and releasing lithium ions, contained together with an electrolyte solution in a container (which may be a laminate film container or the like).

An oxide positive electrode active material with a layered structure or an oxide positive electrode active material with a spinel structure or the like used in ordinary lithium secondary batteries can be used as the positive electrode active material. Examples include positive electrode active materials consisting primarily of lithium-cobalt composite oxides (such as $LiCoO_2$), lithium-nickel composite oxides (typically $LiNiO_2$), lithium-manganese composite oxides (such as $LiMn_2O_4$) and the like. The positive electrode may take the form of such a positive electrode active material, mixed together with a conductive material, binder and the like as necessary to form a positive electrode mixture that is then affixed to a positive electrode collector. A carbon material such as carbon black (acetylene black or the like), or a conductive metal powder such as nickel powder or the like can be used as the conductive material. A fluorine resin such as polyvinylidene fluoride (PVDF), polytetrafluoroethylene (PTFE), ethylene tetrafluoroethylene (ETFE) or the like can preferably be used as the binder. A bar, plate, foil, mesh or the like consisting primarily of aluminum, nickel, titanium, stainless steel or the like can be used as the positive electrode collector.

A carbon material such as natural graphite, mesocarbon microbeads (MCMB), highly oriented pyrolytic graphite (HOPG), hard carbon, soft carbon or the like can be used as the negative electrode active material. Other examples of negative electrode active materials include metal materials such as lithium, tin and the like, alone or as alloys. Other examples include metal oxides (such as $Li_4Ti_6O_{12}$ and other lithium titanates), metal sulfides, metal nitrides and other metal compounds. The negative electrode can take the form of such a negative electrode active material, mixed together with a binder or the like as necessary to form a negative electrode mixture that is then affixed to a negative electrode collector. The binder may be similar to those used for the positive electrode active material. The negative electrode collector can be a bar, plate, foil, mesh or the like consisting primarily of copper, nickel, aluminum, stainless steel or the like.

The electrolyte solution disclosed here can preferably be applied to a lithium secondary battery using a carbon material having at least a partial graphite structure (natural graphite or the like) as the electrode active material of at least one of the positive electrode and negative electrode (typically, of at least the negative electrode). This is because in a lithium secondary battery, such a graphite structure is liable to be damaged using an electrolyte solution comprising a supporting electrolyte dissolved in a $BF_3$-chain ether complex, but this damage can be prevented or controlled with the electrolyte solution of the present invention. Application to a lithium secondary battery provided with an electrode consisting effectively of graphite alone as the negative electrode active material is particularly desirable.

The effective of preventing damage to the graphite structure as discussed above by using the electrolyte solution of the present invention can also be obtained with another electrochemical device (other than a lithium secondary battery) using a carbon material having a graphite structure as an active material.

In a typical configuration of the lithium secondary battery disclosed here, a separator is interposed between the positive electrode and negative electrode. The separator can be similar to the separators used in ordinary lithium secondary batteries. For example, a porous sheet, nonwoven cloth or the like made of a resin such as polyethylene (PE), polypropylene (PP), polyester, cellulose, polyamide or the like can be used. The form (outer shape of the container) of the lithium secondary battery is not particularly limited, but may for example be a cylinder, rectangle, coin shape or the like.

Examples of the present invention are explained below, but the present invention is not limited to what is shown in these specific examples.

EXAMPLE 1

Electrolyte Solutions Using $BF_3$-THP Complex as Solvent 3.00 g of tetrahydropyran (THP) and 3.95 g of $BF_3$-diethyl ether complex were placed in a reaction container, and stirred for 3 days at 45° C. in a flow of nitrogen gas to perform an ether exchange reaction. This was distilled twice under reduced pressure to obtain 3.21 g of $BF_3$-THP complex as a colorless liquid.

Figure 2:
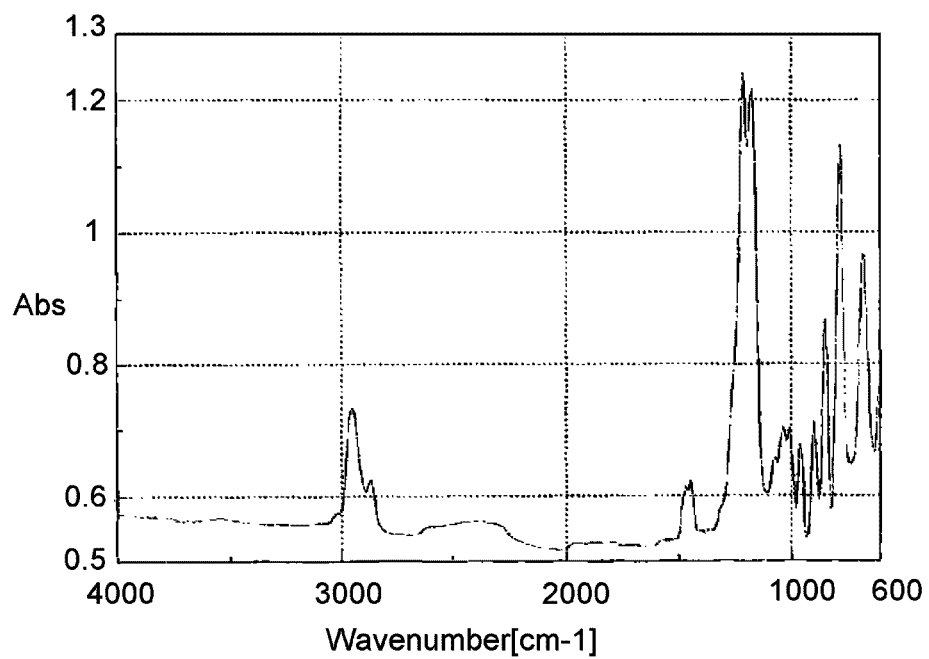
FIG. 2 shows the IR spectrum of a $BF_3$-THP complex.

The resulting $BF_3$-THP complex was subjected to $^1$H-NMR and $^{13}$C-NMR measurement, and synthesis of the target $BF_3$-THP complex was confirmed based on these NMR spectra. The melting point of the $BF_3$-THP complex was −18.2° C. The spectrum data are given below. The results of $^1$H-NMR are also shown in FIG. 1. The results of IR measurement are shown in FIG. 2.

[C7]
$BF_3$-THP
$^1$H-NMR (CDCl$_3$): 4.2 ppm (OCH$_2$CH$_2$CH$_2$), 1.85 ppm (OCH$_2$CH$_2$CH$_2$),
1.73 ppm (OCH$_2$CH$_2$CH$_2$)
$^{13}$C-NMR (CDCl$_3$): 73.3 ppm (OCH$_2$CH$_2$CH$_2$), 24.7 ppm (OCH$_2$CH$_2$CH$_2$),
21.5 ppm (OCH$_2$CH$_2$CH$_2$)

LiPF$_6$ was added to the complex obtained above in a glove box in argon atmosphere, and mixed with stirring for 24 hours to prepare an electrolyte solution of LiPF$_6$ dissolved in the $BF_3$-THP complex at a concentration of 0.5 mol/kg (here and below, sometimes represented as "0.5 M"). An electrolyte solution comprising 0.5 mol/kg of LiTFSI dissolved in the $BF_3$-THP complex was prepared in the same way.

EXAMPLE 2

Electrolyte Solutions Using $BF_3$-THF Complex as Solvent

A commercial boron trifluoride-tetrahydrofuran ($BF_3$-THF) complex was distilled under reduced pressure, processed with metal lithium and purified by rectification. LiPF$_6$ was added to the purified $BF_3$-THF complex (melting point—3.7° C.) in a glove box in argon atmosphere, and mixed with stirring for 24 hours to prepare an electrolyte solution comprising 0.1 mol/kg of LiPF$_6$ dissolved in the $BF_3$-THF complex. An electrolyte solution comprising 0.1 mol/kg of LiBF$_4$ dissolved in the $BF_3$-THF complex was prepared in the same way. Electrolyte solutions comprising LiTFSI dissolved in the $BF_3$-THF complex at concentrations of 0.1 mol/kg, 0.5 mol/kg, 1.0 mol/kg and 2.0 mol/kg were also prepared in the same way.

EXAMPLE 3

Electrolyte Solution Using $BF_3$-2MeTHF Complex as Solvent 5.9 g of 2-methyltetrahydrofuran (2MeTHF) and 10.0 g of $BF_3$-diethyl ether complex were placed in a reaction container, and stirred for 2 days at 40° C. in a flow of nitrogen gas to perform an ether exchange reaction. This was then distilled under reduced pressure, processed with metal lithium and rectified to obtain 4.6 g of $BF_3$-2MeTHF complex as a colorless liquid.

The $^1$H-NMR and $^{13}$C-NMR spectra of the resulting $BF_3$-2MeTHF complex were measured, and synthesis of the target $BF_3$-2MeTHF complex was confirmed from the results. The melting point of this $BF_3$-2MeTHF complex was −37.5° C. The spectrum data are shown below.

[C8]
$BF_3$-2MeTHF
$^1$H-NMR(CDCl$_3$): 4.9 ppm (s:OCHCH$_3$), 4.3 ppm (d:CH$_2$OCHCH$_3$),
2.4 ppm (q:OCHCH$_3$CHH),
2.2 ppm (q:OCHCH$_3$CH$_2$CH$_2$),
1.8 ppm (q:OCH$_2$CH$_3$CHH), 1.48 ppm(d:CH$_2$OCHCH$_3$)
$^{13}$C-NMR(CDCl$_3$): 84.1 ppm (OCH$_2$CH$_3$C), 72.6 ppm (COCHCH$_3$),
32.9 ppm (OCHCH$_3$C), 24.3 ppm (OCHCH$_3$CC),
20.3 ppm (OCHCH$_3$)

LiPF$_6$ was added to the complex obtained above in a glove box in argon atmosphere, and mixed by stirring for 24 hours to obtain an electrolyte solution comprising 0.1 mol/kg of LiPF$_6$ dissolved in the BF$_3$-2MeTHF complex. An electrolyte solution comprising 0.5 mol/kg of LiTFSI dissolved in the BF$_3$-2MeTHF complex was also prepared in the same way.

TABLE 1

| Solvent | Supporting electrolyte | Supporting electrolyte concentration [mol/kg] | Abbreviation |
|---|---|---|---|
| THP | LiPF$_6$ | 0.5 | 0.5M LiPF$_6$ THP•BF$_3$ |
| THP | LiTFSI | 0.5 | 0.5M LiTFSI THP•BF$_3$ |
| THF | LiPF$_6$ | 0.1 | 0.1M LiPF$_6$ THF•BF$_3$ |
| THF | LiTFSI | 0.1 | 0.1M LiTFSI THF•BF$_3$ |
| THF | LiTFSI | 0.5 | 0.5M LiTFSI THF•BF$_3$ |
| THF | LiTFSI | 1.0 | 1.0M LiTFSI THF•BF$_3$ |
| THF | LiTFSI | 2.0 | 2.0M LiTFSI THF•BF$_3$ |
| THF | LiBF$_4$ | 0.1 | 0.1M LiBF$_4$ THF•BF$_3$ |
| 2MeTHF | LiPF$_6$ | 0.1 | 0.1M LiPF$_6$ 2MeTHF•BF$_3$ |
| 2MeTHF | LiTFSI | 0.5 | 0.5M LiTFSI 2MeTHF•BF$_3$ |

[Evaluation of Electrochemical Stability]

Of the electrolyte solutions prepared in Examples 1 through 3 (see Table 1), the oxidation potential of those electrolyte solutions containing LiPF$_6$ as a supporting electrolyte was measured. Oxidation potential was measured by the linear sweep voltammetry method using a sealed two-electrode cell with platinum for the working electrode and metal lithium for the counter-electrode and reference electrode. During measurement, the potential of the working electrode was swept from corrosion potential to high potential. The measurement temperature was 30° C., and the sweep rate was 0.1 mV/second. Electrolyte solutions with the corresponding cyclic ether substituted for the BF$_3$-cyclic ether complex as the solvent were prepared as controls, and oxidation potential was measured in the same way. The results are shown in Table 2.

TABLE 2

| BF$_3$-cyclic ether complex | Oxidation potential | Cyclic ether | Oxidation potential |
|---|---|---|---|
| BF$_3$-THF | 4.8 V | THF | 4.3 V |
| BF$_3$-2MeTHF | 5.3 V | 2MeTHF | 4.7 V |
| BF$_3$-THP | 5.5 V | THP | 5.3 V |

As shown in Table 2, oxidation potential was much higher with a BF$_3$ complex of a THF, 2MeTHF or THP cyclic ether than with the corresponding cyclic ether (control). In other words, electrochemical stability was improved. In particular, the BF$_3$ complexes of 2MeTHF and THP had oxidation resistance in excess of 5 V. These results suggest that these complexes can be used for electrolyte solutions in 5 V secondary batteries. The BF$_3$ complex of 2MeTHF, which has a structure with a methyl group introduced into the second position of the ether ring of THF, was confirmed to exhibit higher oxidation resistance than the BF$_3$ complex of THF.

[Evaluating Ion Conductivity]

Figure 3:
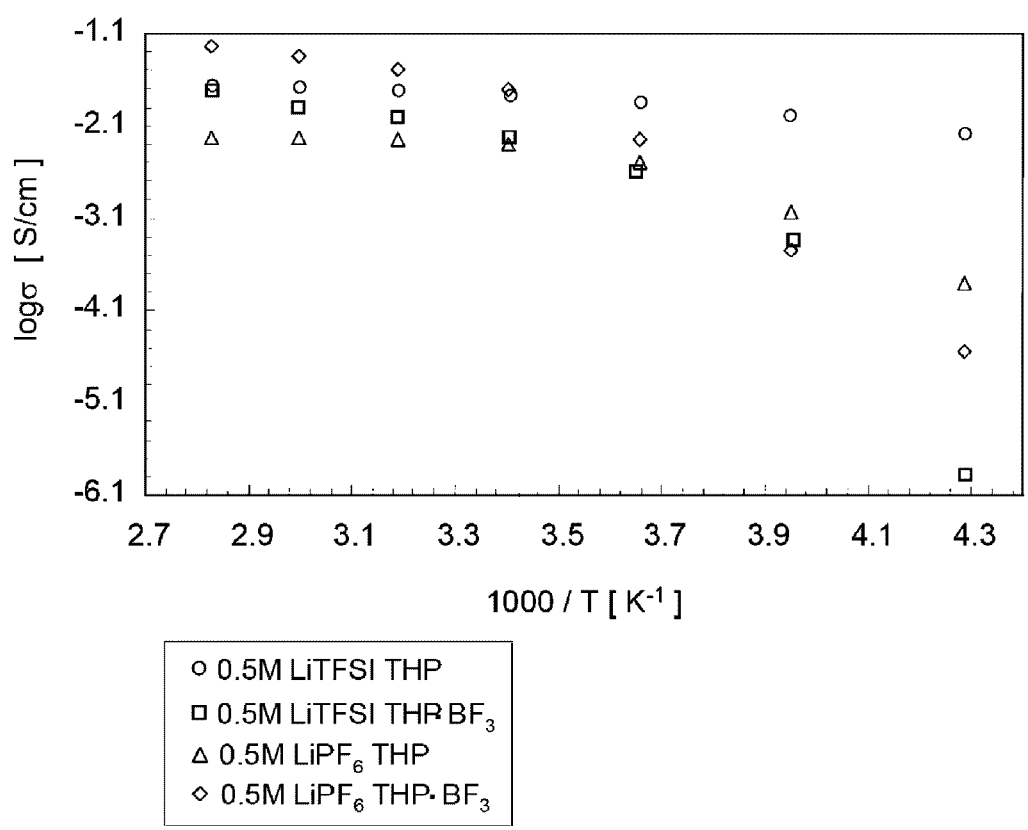
FIG. 3 is a graph showing the ion conductivity of an electrolyte solution in which the principal solvent is a $BF_3$-THP complex.

The ion conductivity σ (S/cm) of the electrolyte solutions prepared in Example 1 was measured. Measurement was carried out by the AC impedance method using a sealed two-electrode cell provided with a stainless steel (SUS) electrode. The measurement temperature was raised in stages, and ion conductivity was measured at each temperature. The ion conductivity of electrolyte solutions having the corresponding cyclic ether substituted for the BF$_3$-cyclic ether as the solvent in the solution was measured in the same way. The results are shown in the tables below, and in FIG. 3.

TABLE 3

0.5 mol/kg LiPF$_6$ THP•BF$_3$

| T [° C.] | σ [mS/cm] |
|---|---|
| −40 | 0.01 |
| −21 | 0.46 |
| 1 | 2.43 |
| 20 | 5.85 |
| 40 | 9.52 |
| 60 | 12.6 |
| 80 | 19.1 |

TABLE 4

0.5 mol/kg LiTFSI THP•BF$_3$

| T [° C.] | σ [mS/cm] |
|---|---|
| −40 | 0.03 |
| −20 | 0.35 |
| 0.2 | 5.64 |
| 21 | 19.9 |
| 40 | 32.6 |
| 60 | 43.7 |
| 80 | 56.0 |

TABLE 5

0.5 mol/kg LiPF$_6$ THP

| T [° C.] | σ [mS/cm] |
|---|---|
| −40 | 6.54 |
| −20 | 10.3 |
| 0 | 13.8 |
| 20 | 16.5 |
| 40 | 18.8 |
| 60 | 20.5 |
| 80 | 21.3 |

TABLE 6

0.5 mol/kg LiTFSI THP

| T [° C.] | σ [mS/cm] |
|---|---|
| −40 | 0.16 |
| −20 | 0.92 |
| 0.2 | 3.12 |
| 21 | 5.08 |
| 40 | 5.57 |
| 60 | 5.86 |
| 80 | 5.92 |

As shown in these tables and figures, an electrolyte solution comprising 0.5 M LiPF$_6$ dissolved in BF$_3$-THP exhibited relatively good ion conductivity even though the melting point of BF$_3$-THP is relatively high (−18.2° C.), with ion conductivity σ being on the order of $10^{-1}$ mS/cm even at −20° C. An electrolyte solution comprising 0.5 M LiTFSI dissolved in BF$_3$-THP exhibited ion conductivity σ even higher than that of a common conventional lithium secondary battery electrolyte solution using an EC-DEC solvent, on the order of 10 mS/cm at a temperature range of room temperature and above.

Figure 4:
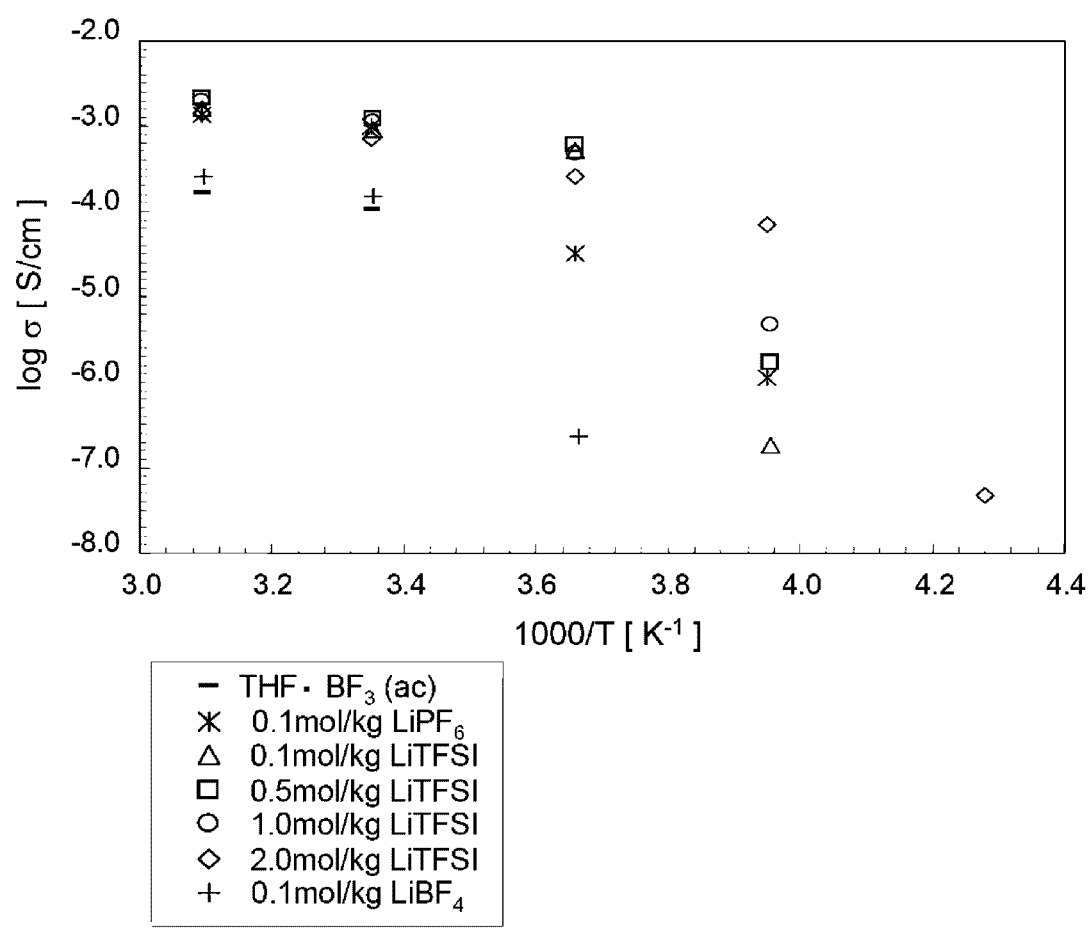
FIG. 4 is a graph showing the ion conductivity of an electrolyte solution in which the principal solvent is a $BF_3$-THF complex.

The ion conductivity σ [S/cm] of the electrolyte solutions prepared in Example 2 was measured in the same way. The ion conductivity σ of a $BF_3$-THF complex containing no supporting electrolyte was also measured as a control. The results are shown in the following tables and in FIG. 4.

TABLE 7

0.1 mol/kg $LiPF_6$ THF•$BF_3$

| T [° C.] | σ [mS/cm] |
|---|---|
| −40 | $1.2 \times 10^{-4}$ |
| −20 | $7.5 \times 10^{-3}$ |
| 0.2 | 1.2 |
| 25 | 2.1 |
| 50 | 3.2 |

TABLE 8

0.5 mol/kg LiTFSI THF•$BF_3$

| T [° C.] | σ ]mS/cm] |
|---|---|
| −20 | $1.7 \times 10^{-3}$ |
| 0.0 | 0.61 |
| 25 | 1.21 |
| 50 | 2.13 |

TABLE 9

0.1 mol/kg $LiBF_6$ THF•$BF_3$

| T [° C.] | σ [mS/cm] |
|---|---|
| −0.3 | $1.2 \times 10^{-4}$ |
| 25 | 0.16 |
| 50 | 0.27 |

TABLE 10

THF•$BF_3$

| T [° C.] | σ [mS/cm] |
|---|---|
| 25 | 0.11 |
| 50 | 0.16 |

As shown in these tables and figures, an electrolyte solution comprising 0.1 M $LiPF_6$ dissolved in $BF_3$-THF exhibited relatively good ion conductivity despite the relatively low lithium salt concentration, with ion conductivity σ being 2.1 mS/cm at 25° C. The electrolyte solutions comprising 0.1 M lithium salts dissolved in $BF_3$-THF had much lower ion conductivity in the low temperature range. This is attributed to the fact that $BF_3$-THF has a relatively high melting point of −3.7° C. The low-temperature characteristics also tended to improve due to a drop in the coagulation point as the concentration of the lithium salt increased. The ion conductivity σ of an electrolyte solution of 2.0 M LiTFSI dissolved in $BF_3$-THF was $2.4 \times 10^{-1}$ mS/cm at −20° C., higher than that of a common conventional lithium secondary battery electrolyte solution using an EC-DEC solvent.

Figure 5:
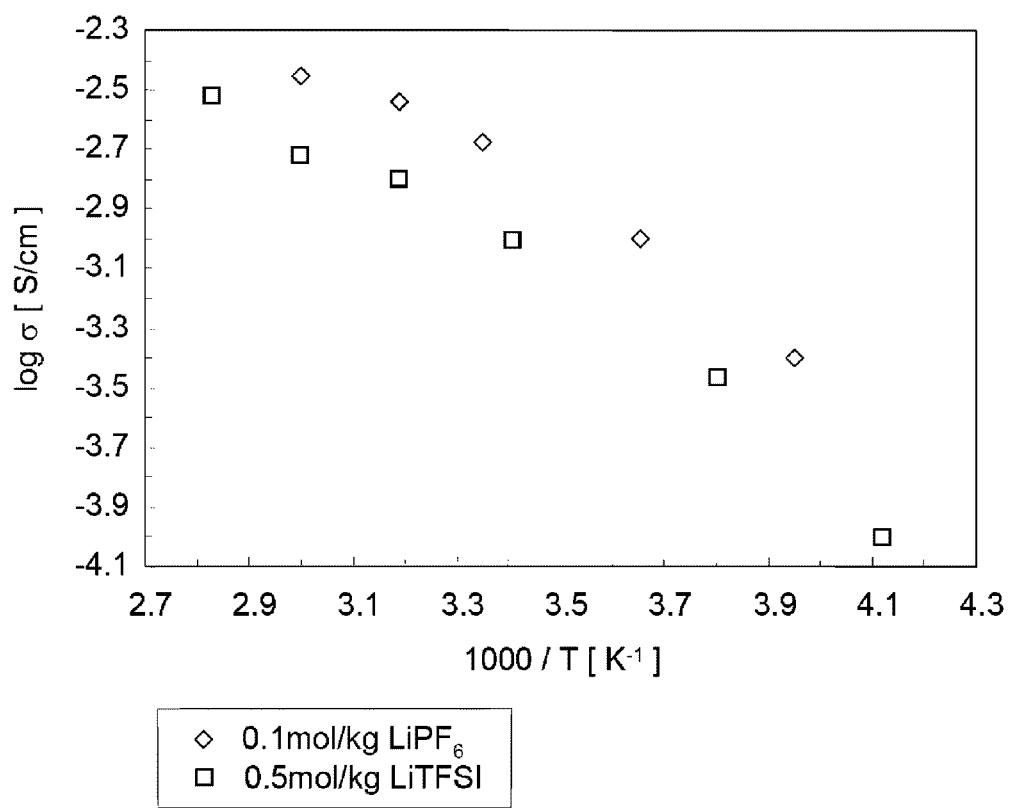
FIG. 5 is a graph showing the ion conductivity of an electrolyte solution in which the principal solvent is a $BF_3$-2MeTHF complex.

The ion conductivity σ [S/cm] of the electrolyte solutions prepared in Example 3 was also measured in the same way. The results are shown in the following tables and in FIG. 5.

TABLE 11

0.1 mol/kg $LiPF_6$ 2-MeTHF•$BF_3$

| T [° C.] | σ [mS/cm] |
|---|---|
| −20.0 | 0.4 |
| 0.6 | 1.0 |
| 25.4 | 2.1 |
| 40.5 | 2.9 |
| 60.2 | 3.5 |

TABLE 12

0.5 mol/kg LiTFSI 2-MeTHF•$BF_3$

| T [° C.] | σ [mS/cm] |
|---|---|
| −30.5 | 0.1 |
| −10.2 | 0.3 |
| 20.2 | 1.0 |
| 40.5 | 1.6 |
| 60.3 | 1.9 |
| 80.3 | 3.0 |

As shown in these tables and figures, the electrolyte solutions using $BF_3$-2MeTHF as the solvent exhibited relatively high ion conductivity, with ion conductivity σ being on the order of 10 mS/cm at temperatures of 0° C. or more, and on the order of $10^{-1}$ mS/cm at temperatures of −10° C. or less. The electrolyte solution comprising 1 M $LiPF_6$ dissolved in $BF_3$-2MeTHF exhibited relativity good ion conductivity of 2.1 mS/cm at 25° C. despite the relatively low lithium salt concentration. The reason why the ion conductivity of the electrolyte solutions using $BF_3$-2MeTHF as the solvent was higher than the ion conductivity of the electrolyte solutions using $BF3_3$-THF as the solvent is probably related to the fact that the melting point of $BF_3$-2MeTHF (−37.5° C.) is much lower than that of $BF_3$-THF (−3.7° C.).

[Observation of Graphite Structure]

$LiCoO_2$ as the positive electrode active material was mixed with N-methylpyrrolidone (NMP) together with carbon black (CB) and polyvinylidene fluoride (PVDF) to prepare a positive electrode composite paste. This was applied to aluminum foil (positive electrode collector) and dried to prepare a positive electrode sheet having a positive electrode active material layer on one side of the collector. This positive electrode sheet was punched out to a specific size for the positive electrode.

Graphite as the negative electrode active material was mixed with NMP together with PVDF to prepare a negative electrode composite paste. This was applied to copper foil (negative electrode collector) and dried to prepare a negative electrode sheet having a negative electrode active material layer on one side of the collector. This negative electrode sheet was punched out to a specific size for the negative electrode.

DMC was added to the 0.5 M LiTFSI THP.$BF_3$ prepared in Example 1 to prepare an electrolyte solution (electrolyte solution A) containing 10 mass % DMC. The positive electrode and negative electrode were arranged opposite each other with a separator (a porous polypropylene sheet in this case) in between, and contained in a stainless steel container together with electrolyte solution A to construct a coin-shaped (2032 type) lithium ion battery 20 mm in diameter and 3.2 mm thick.

Figure 6:
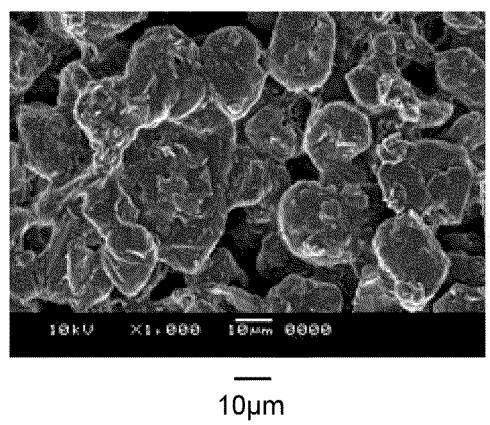
FIG. 6 is an SEM image of a graphite surface after charge and discharge of a cell constructed using an electrolyte solution in which the principal solvent is a $BF_3$-THP complex.

This lithium ion battery was subjected to 3 charge-discharge cycles under conditions of current density 0.57 mA/cm², 0.5 C, cut-off voltage 4.2 V-2.5 V. The battery was then disassembled, and the surface condition of the negative electrode active material layer was observed under a scanning electron microscope (SEM). FIG. 6 shows the resulting SEM image.

Figure 7:
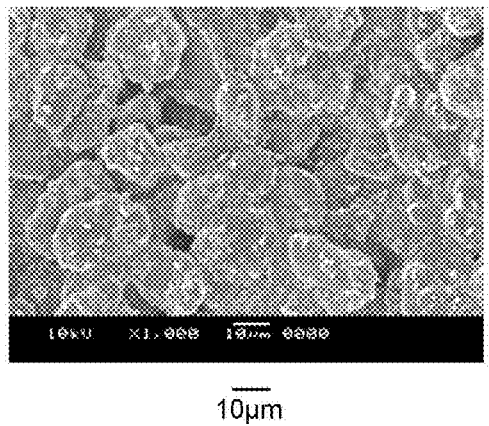
FIG. 7 is an SEM image of a graphite surface after charge and discharge of a cell constructed using an electrolyte solution in which the principal solvent is a $BF_3$-THF complex.

DMC was added to the 1.0 M LiTFSI THF.BF$_3$ electrolyte solution prepared in Example 2 to prepare a 1.0 M LiTFSI THF.BF$_3$ electrolyte solution (electrolyte solution B) containing 10 mass % DMC. 3 cycles of charge and discharge were performed as above but using electrolyte solution B in place of electrolyte solution A, and the surface condition of the negative electrode active material layer was observed under a SEM. FIG. 7 shows the resulting SEM image.

Figure 8:
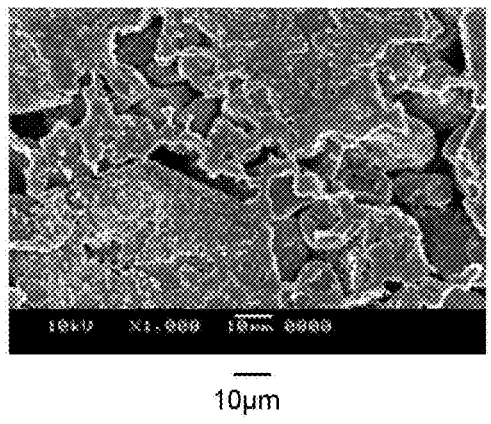
FIG. 8 is an SEM image of a graphite surface after charge and discharge of a cell constructed using an electrolyte solution in which the principal solvent is a $BF_3$-diethyl ether complex.

LiTFSI was added to and mixed with a BF$_3$-diethyl ether (Et$_2$O) complex to prepare a solution of 1.0 M LiTFSI dissolved in the BF$_3$-diethyl ether complex (1.0 M LiTFSI Et$_2$O.BF$_3$). DMC was added to this solution to prepare a 1.0 M LiTFSI Et$_2$O.BF$_3$ solution containing 10 mass % DMC (electrolyte solution C). 3 cycles of charge-discharge were performed as above except using electrolyte solution C in place of electrolyte solution A, and the surface condition of the negative electrode active material layer was observed by SEM. FIG. 8 shows the resulting SEM image.

As shown in FIG. 8, using an electrolyte solution having a BF$_3$-chain ether complex (BF$_3$-diethyl ether complex in this case) as the principal solvent, damage (surface peeling) of the graphite structure was observed in the negative electrode active material layer after charge-discharge. By contrast, as shown in FIGS. 6 and 7, using electrolyte solutions A and B having BF$_3$-cyclic ether complexes as the principal solvents, there was no peeling of the graphite structure of the negative electrode active material layer after charge-discharge, and the shape of the graphite particles appears clearly. That is, damage to the graphite structure was prevented by using a BF$_3$-cyclic ether complex as the principal solvent of the electrolyte solution instead of a BF$_3$-chain ether complex.

Specific examples of the present invention were explained in detail above, but these are only examples, and the scope of the claims is not limited thereby. The technology described in the claims encompasses various changes and modifications to the specific examples given above.

The invention claimed is:

1. An electrochemical device using a carbon material having a graphite structure as an active material, the device comprising an electrolyte solution containing a solvent and a supporting electrolyte, wherein
the principal constituent of the solvent is a BF$_3$-cyclic ether complex,
the supporting electrolyte is a lithium salt chosen from LiPF$_6$, LiBF$_4$, LiN(SO$_2$CF$_3$)$_2$, LiN(SO$_2$C$_2$F$_5$)$_2$, LiCF$_3$SO$_3$, LiC$_4$F$_9$SO$_3$, LiC(SO$_2$CF$_3$)$_3$, and LiClO$_4$, and
the BF$_3$-cyclic ether complex is chosen from the group consisting of the following formulae (1) to (4):

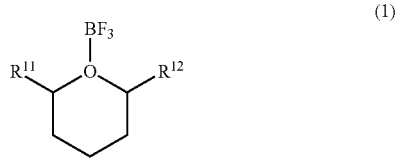

(1)

wherein in the formula (1), R$^{11}$ is chosen from C$_{1-3}$ alkyl groups and C$_{1-3}$ alkoxy groups, and R$^{12}$ is chosen from a hydrogen atom and C$_{1-3}$ alkyl groups and C$_{1-3}$ alkoxy groups;

(2)

wherein in the formula (2), R$^{13}$ is chosen from C$_{1-3}$ alkyl groups;

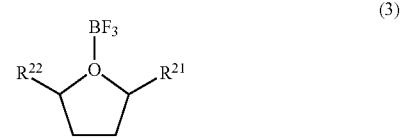

(3)

wherein in the formula (3), R$^{21}$ is chosen from C$_{1-3}$ alkyl groups and C$_{1-3}$ alkoxy groups, and R$^{22}$ is chosen from a hydrogen atom and C$_{1-3}$ alkyl groups and C$_{1-3}$ alkoxy groups; and

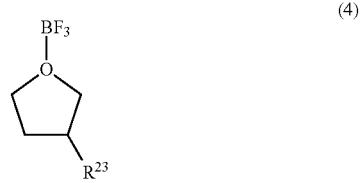

(4)

wherein in the formula (4), R$^{23}$ is chosen from C$_{1-3}$ alkyl groups.

2. The electrochemical device according to claim 1, wherein the cyclic ether is 2-methyltetrahydrofuran.

3. The electrochemical device according to claim 1, configured as a lithium secondary battery.

4. An electrochemical device comprising:
a negative electrode comprising a carbon material having a graphite structure as a negative electrode active material, and
an electrolyte solution containing a solvent and a supporting electrolyte, wherein
the principal constituent of the solvent is a BF$_3$-cyclic ether complex,
the supporting electrolyte is a lithium salt chosen from LiPF$_6$, LiBF$_4$, LiN(SO$_2$CF$_3$)$_2$, LiN(SO$_2$C$_2$F$_5$)$_2$, LiCF$_3$SO$_3$, LiC$_4$F$_9$SO$_3$, LiC(SO$_2$CF$_3$)$_3$, and LiClO$_4$, and
the BF$_3$-cyclic ether complex is chosen from the group consisting of the following formulae (1) to (6):

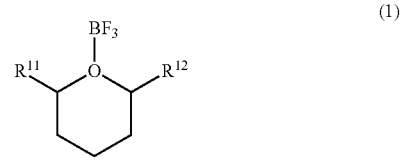

(1)

wherein in the formula (1), R$^{11}$ is chosen from C$_{1-3}$ alkyl groups and C$_{1-3}$ alkoxy groups, and R$^{12}$ is chosen from a hydrogen atom and C$_{1-3}$ alkyl groups and C$_{1-3}$ alkoxy groups;

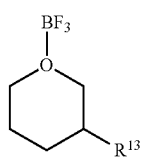

(2)

wherein in the formula (2), $R^{13}$ is chosen from $C_{1-3}$ alkyl groups;

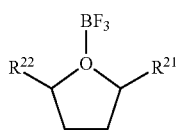

(3)

wherein in the formula (3), $R^{21}$ is chosen from $C_{1-3}$ alkyl groups and $C_{1-3}$ alkoxy groups, and $R^{22}$ is chosen from a hydrogen atom and $C_{1-3}$ alkyl groups and $C_{1-3}$ alkoxy groups; and

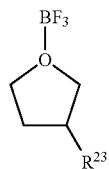

(4)

wherein in the formula (4), $R^{23}$ is chosen from $C_{1-3}$ alkyl groups;

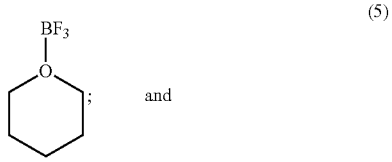

(5)

and

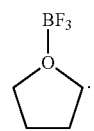

(6)

5. The electrochemical device according to claim 4, wherein the cyclic ether is tetrahydropyran.

6. The electrochemical device according to claim 4, wherein the cyclic ether is 2-methyltetrahydrofuran.

7. The electrochemical device according to claim 4, further comprising a positive electrode comprising an oxide positive electrode active material with a layered structure or an oxide positive electrode active material with a spinel structure.

8. The electrochemical device according to claim 2, configured as a lithium secondary battery.

9. The electrochemical device according to claim 1, wherein the lithium salt is $LiBF_4$.

10. The electrochemical device according to claim 4, wherein the lithium salt is $LiBF_4$.

* * * * *